US012421484B2

(12) United States Patent
Larkin et al.

(10) Patent No.: US 12,421,484 B2
(45) Date of Patent: Sep. 23, 2025

(54) BIOREACTOR ASSEMBLY, BIOREACTOR, AND METHOD OF OPERATING SAME

(71) Applicants: The Regents of the University of Michigan, Ann Arbor, MI (US); STEL TECHNOLOGIES, LLC, Ann Arbor, MI (US)

(72) Inventors: Lisa M. Larkin, Ann Arbor, MI (US); Ellen M. Arruda, Ann Arbor, MI (US); Michael J. Smietana, Memphis, TN (US); Pablo Moncado-Larrotiz, San Francisco, CA (US); Haley Titinger, Ann Arbor, MI (US)

(73) Assignees: The Regents of the University of Michigan, Ann Arbor, MI (US); STEL TECHNOLOGIES, LLC, Ann Arbor, MI (US)

( * ) Notice: Subject to any disclaimer, the term of this patent is extended or adjusted under 35 U.S.C. 154(b) by 974 days.

(21) Appl. No.: 17/614,257

(22) PCT Filed: May 24, 2020

(86) PCT No.: PCT/US2020/034443
§ 371 (c)(1),
(2) Date: Nov. 24, 2021

(87) PCT Pub. No.: WO2020/243035
PCT Pub. Date: Dec. 3, 2020

(65) Prior Publication Data
US 2022/0243156 A1 Aug. 4, 2022

Related U.S. Application Data

(60) Provisional application No. 62/852,715, filed on May 24, 2019.

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/02* (2013.01); *C12M 23/22* (2013.01); *C12M 25/04* (2013.01);
(Continued)

(58) Field of Classification Search
CPC ...... C12M 21/08; C12M 23/02; C12M 23/22; C12M 25/04; C12M 29/10; C12M 29/20; C12M 35/08
See application file for complete search history.

(56) References Cited

U.S. PATENT DOCUMENTS

2002/0173033 A1  11/2002  Hammerick
2005/0260745 A1  11/2005  Domansky et al.
(Continued)

FOREIGN PATENT DOCUMENTS

JP   2010063379 A   3/2010
WO  2005123950 A2  12/2005

OTHER PUBLICATIONS

International Search Report corresponding to International Application No. PCT/US2020/034443, dated Mar. 29, 2021, 3 pages.
(Continued)

*Primary Examiner* — John McGuirk
(74) *Attorney, Agent, or Firm* — Reising Ethington P.C.

(57) ABSTRACT

A bioreactor capable of producing complex, three-dimensional tissue constructs has improved media transfer and increased controllability with regard to exposure to the external environment. The bioreactor includes an external surface, a first tissue culture side for culturing a first cell source in a first tissue culture support region, a second tissue
(Continued)

culture side for culturing a second cell source in a second tissue culture support region, and a plurality of ports. At least one of the ports of the plurality of ports extend from the first tissue culture support region of the first tissue culture side to the external surface. The plurality of ports can include an external port that is configured to be a liquid inlet when the bioreactor is in a first orientation and a gas outlet when the bioreactor is in a second orientation.

14 Claims, 10 Drawing Sheets

(51) Int. Cl.
  *C12M 1/12* (2006.01)
  *C12M 1/42* (2006.01)
(52) U.S. Cl.
  CPC ............ *C12M 29/10* (2013.01); *C12M 29/20* (2013.01); *C12M 35/08* (2013.01)

(56) References Cited

U.S. PATENT DOCUMENTS

| | | | |
|---|---|---|---|
| 2007/0166819 A1* | 7/2007 | Ghosh | C12M 23/10 435/305.4 |
| 2010/0311158 A1 | 12/2010 | Kang | |
| 2014/0342447 A1* | 11/2014 | Aviles | C12M 25/02 435/297.1 |
| 2015/0247112 A1* | 9/2015 | Orr | C12M 29/10 435/395 |
| 2017/0037354 A1 | 2/2017 | Larkin et al. | |
| 2020/0199504 A1* | 6/2020 | Timmins | C12M 41/44 |

OTHER PUBLICATIONS

Written Opinion corresponding to International Application No. PCT/US2020/034443, dated Mar. 29, 2021, 4 pages.

* cited by examiner

BIOREACTOR ASSEMBLY, BIOREACTOR, AND METHOD OF OPERATING SAME

GOVERNMENT FUNDING

This invention was made with government support under grant contract number 1448937 awarded by the National Science Foundation (NSF). The government has certain rights in the invention.

FIELD

This invention relates generally to bioreactors, and more particularly to bioreactors that facilitate the formation of complex three-dimensional and multi-phasic tissue constructs.

BACKGROUND

A bioreactor, such as the bioreactor described in U.S. application Ser. No. 15/211,501 filed. Jul. 15, 2016 (now U.S. Pat. No. 10,167,444), which is incorporated by reference herein in its entirety, can allow for the production of complex three-dimensional tissue constructs. With such bioreactors, improved media transfer is desirable, as it can help facilitate improved growth of the three-dimensional tissue construct. Further, more precise control of exposure to the external environment can help with various aspects including portability, such as when the tissue construct is transported to the operating room in advance of a surgical procedure.

SUMMARY

According to one embodiment, there is a bioreactor, comprising: an external surface; a first tissue culture side for culturing a first cell source in a first tissue culture support region; a second tissue culture side for culturing a second cell source in a second tissue culture support region; and a plurality of ports. At least one of the ports of the plurality of ports extends from the first tissue culture support region of the first tissue culture side to the external surface.

According to various implementations, the bioreactor may further include the following features or any technically-feasible combination of some or all of these features:
  the plurality of ports includes an external port that is configured to be a liquid inlet when the bioreactor is in a first orientation and a gas outlet when the bioreactor is in a second orientation;
  the external port opens from the external surface into a perimeter channel;
  the first tissue culture side and the second tissue culture side are made from a transparent plastic material;
  the first tissue culture support region includes a first tissue culture support surface and the second tissue culture support region includes a second tissue culture support surface;
  the first tissue culture support surface supports two or more separate tissue culture plates and the second tissue culture support surface supports a single tissue culture plate;
  two media collection reservoirs are situated below the two or more separate tissue culture plates;
  the two media collection reservoirs include corner projections to help stabilize or position the two or more separate tissue culture plates;
  the two or more separate tissue culture plates are joined to the single tissue culture plate with a plurality of interiorly extending tissue guides;
  the interiorly extending tissue guides are angled such that a distance between the interiorly extending tissue guides is greater at the two or more separate tissue culture plates than a distance between the interiorly extending tissue guides at the single tissue culture plate;
  the first tissue culture support surface is a doubly recessed area that includes a port side wall having port openings from the plurality of ports;
  the port side wall recesses the first tissue culture support surface away from a sloped media support surface;
  the sloped media support surface has four angled walls that converge toward the first tissue culture support surface;
  an angle of each angled wall of the four angled walls is between 3° and 10°, inclusive;
  the plurality of ports includes feeding ports and seeding ports, and the seeding ports are located closer to the sloped media support surface than the feeding ports;
  the plurality of ports includes an internal port that extends partly into the first tissue culture side or the second tissue culture side to house a non-invasive sensor; and/or
  the first tissue culture side includes a lid recess to accommodate an extending ridge on the second tissue culture side.

According to another embodiment, there is provided a bioreactor, comprising: an external surface; a tissue culture side; and an external port extending between the tissue culture side and the external surface. The external port is configured to be a liquid inlet when the bioreactor is in a first orientation and a gas outlet when the bioreactor is in a second orientation.

According to another embodiment, there is provided a bioreactor, comprising: a tissue culture support region having a media collection reservoir, wherein the media collection reservoir is configured to accommodate at least a portion of an interiorly extending tissue guide.

According to another embodiment, there is provided a bioreactor comprising a first tissue culture side for culturing a first cell source; a second tissue culture side for culturing a second cell source; and a sloped media support surface. The sloped media support surface converges toward a tissue culture support surface in the first tissue culture side or the second tissue culture side.

It is contemplated that any number of the individual features of the above-described embodiments and of any other embodiments depicted in the drawings or description below can be combined in any combination to define an invention, except where features are incompatible.

DRAWINGS

Example embodiments will hereinafter be described in conjunction with the appended drawings, wherein like designations denote like elements, and wherein.

Figure 1:
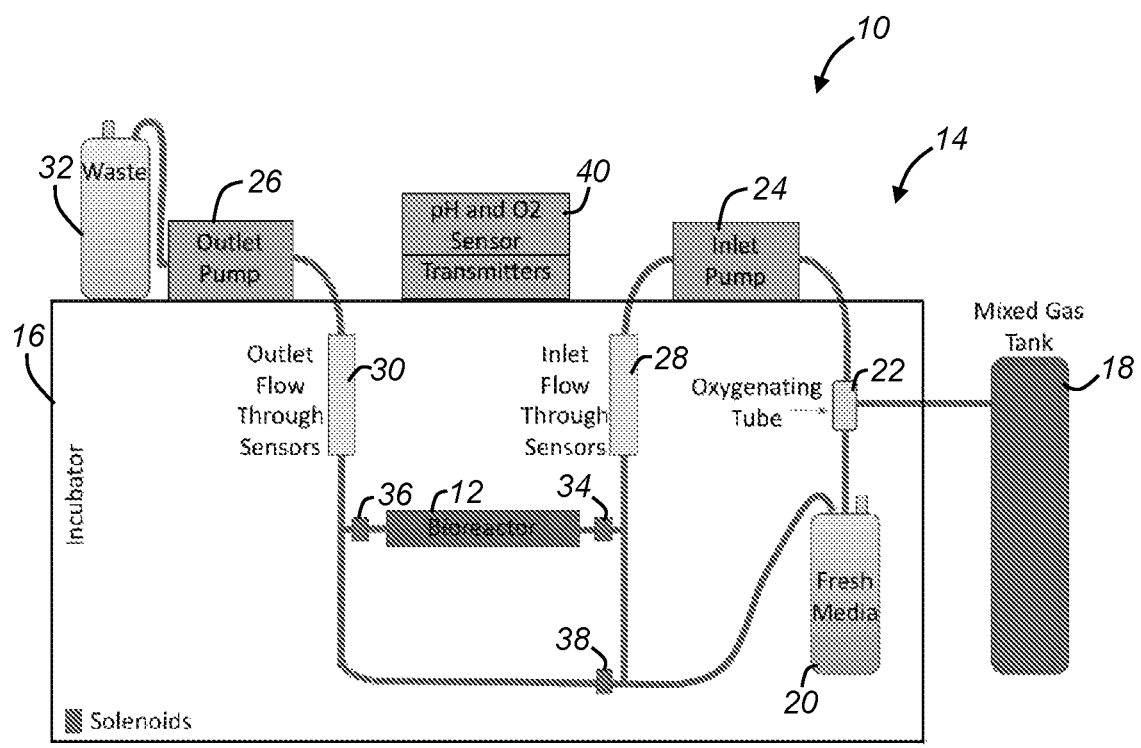
FIG. 1 is schematic representation of a bioreactor assembly and bioreactor in accordance with one embodiment.
Figure 2:
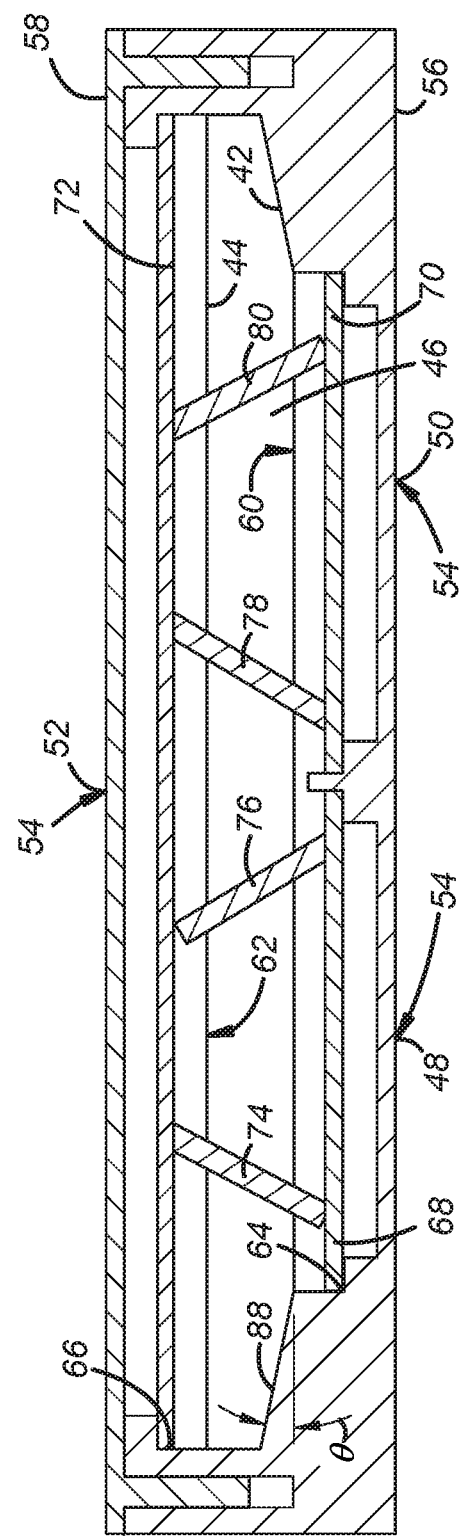
FIG. 2 is cross-section view of the bioreactor of FIG. 1.
Figure 3:
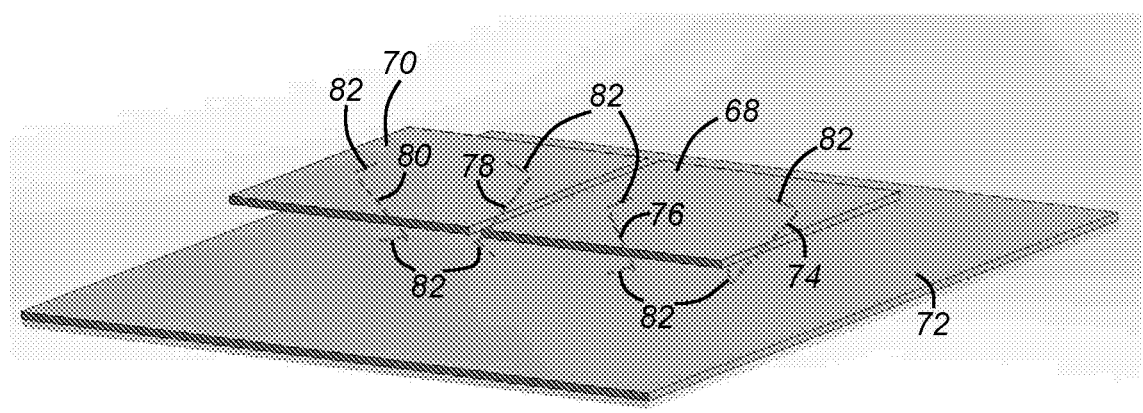
Figure 4:
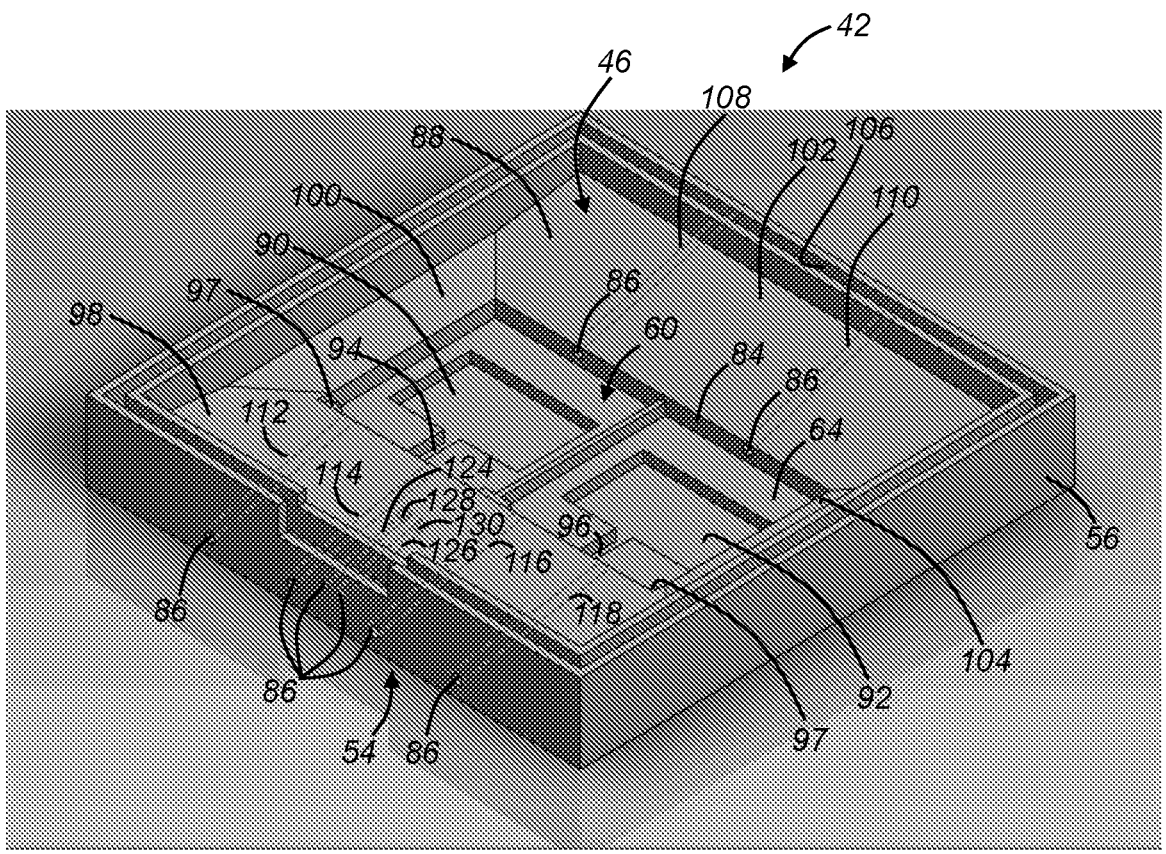
Figure 5:
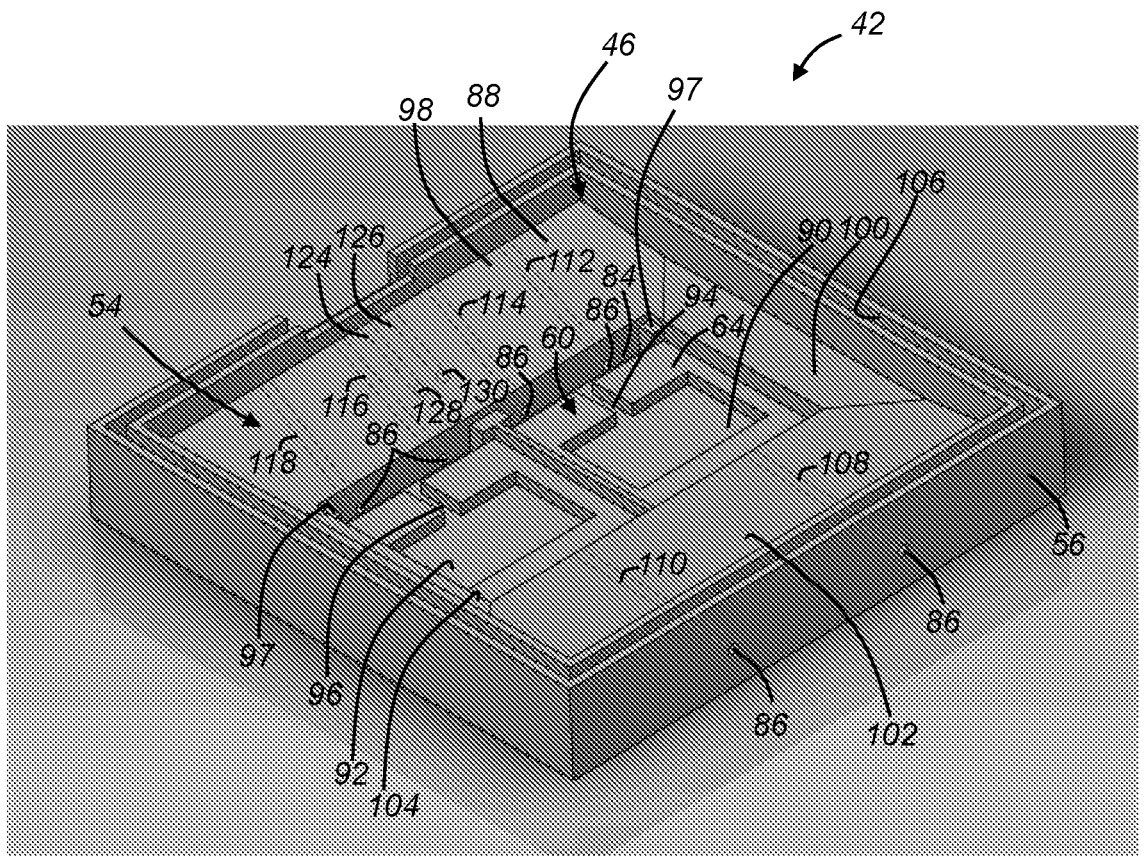
Figure 6:
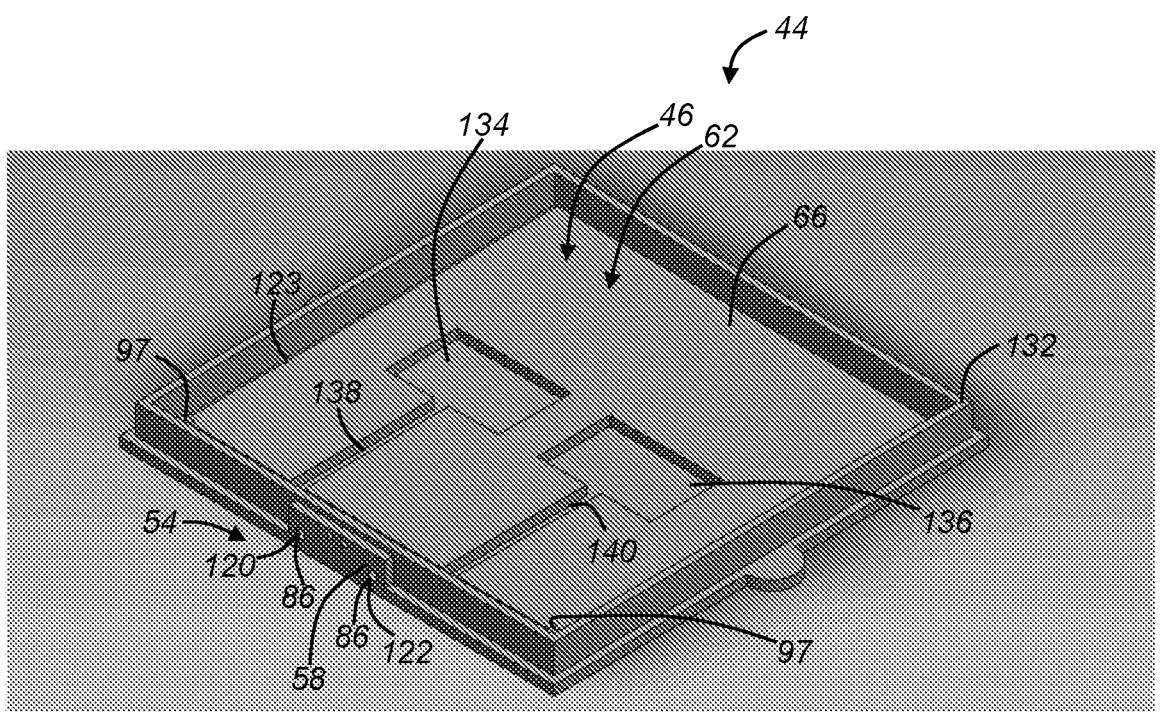
Figure 7:
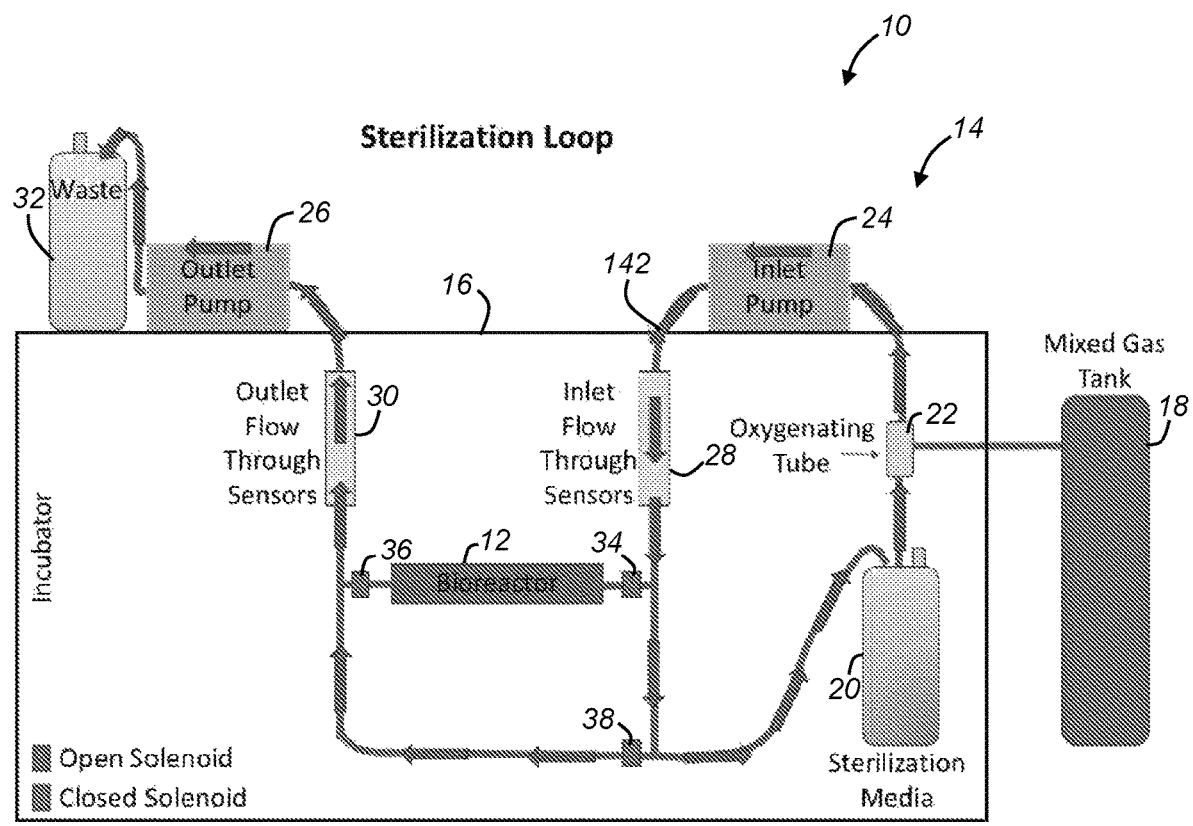
Figure 8:
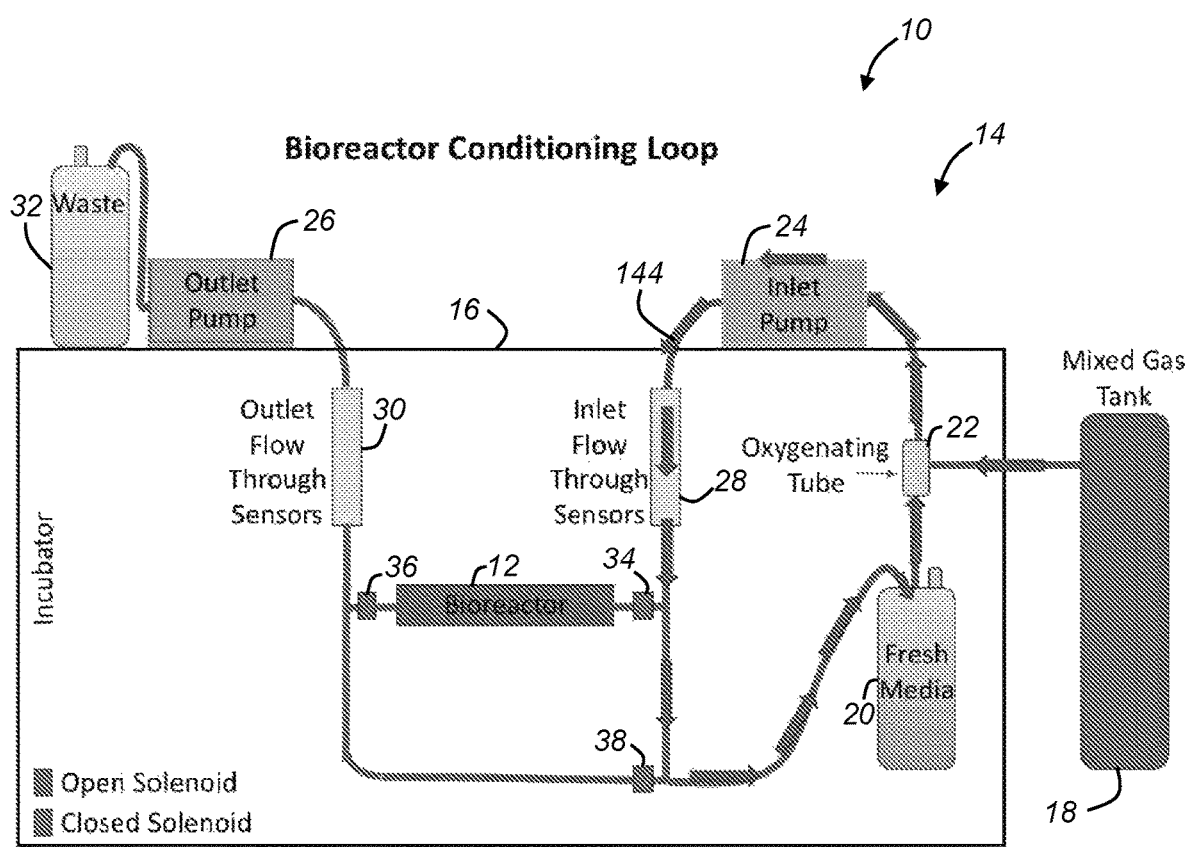
Figure 9:
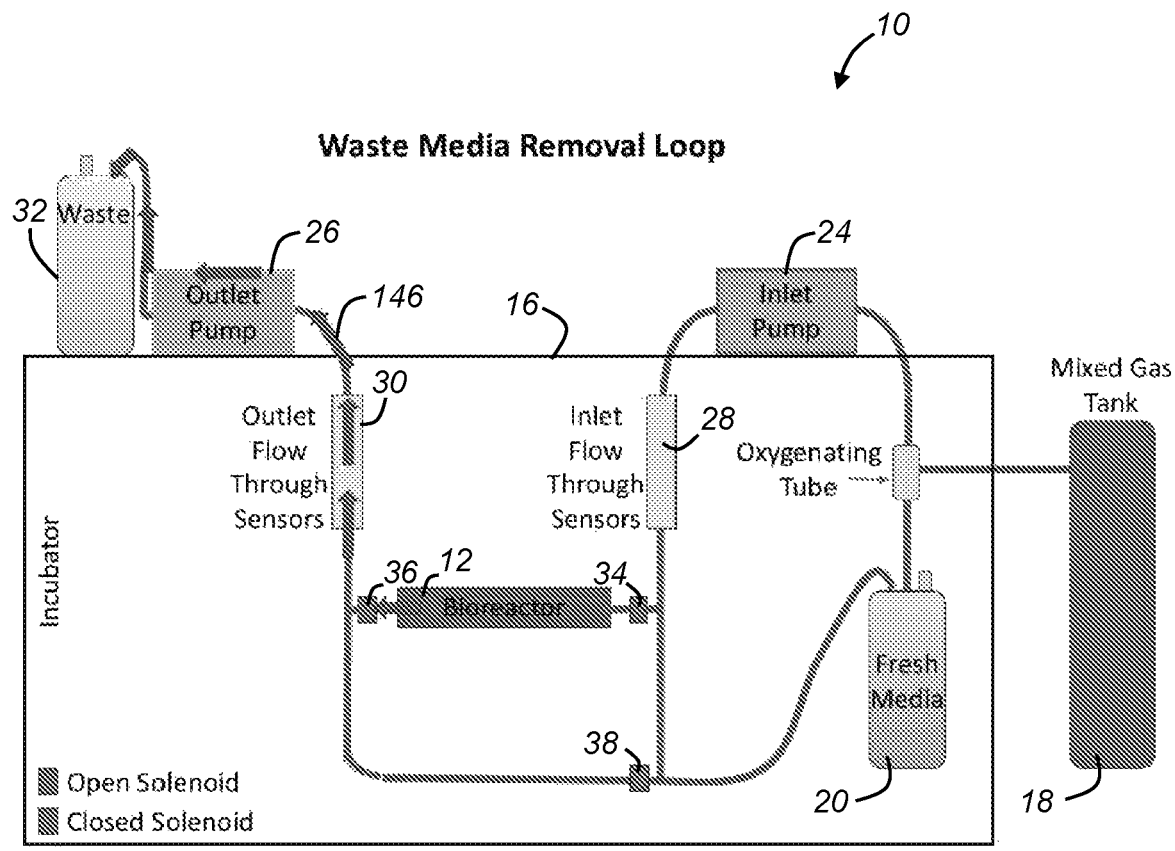
Figure 10:
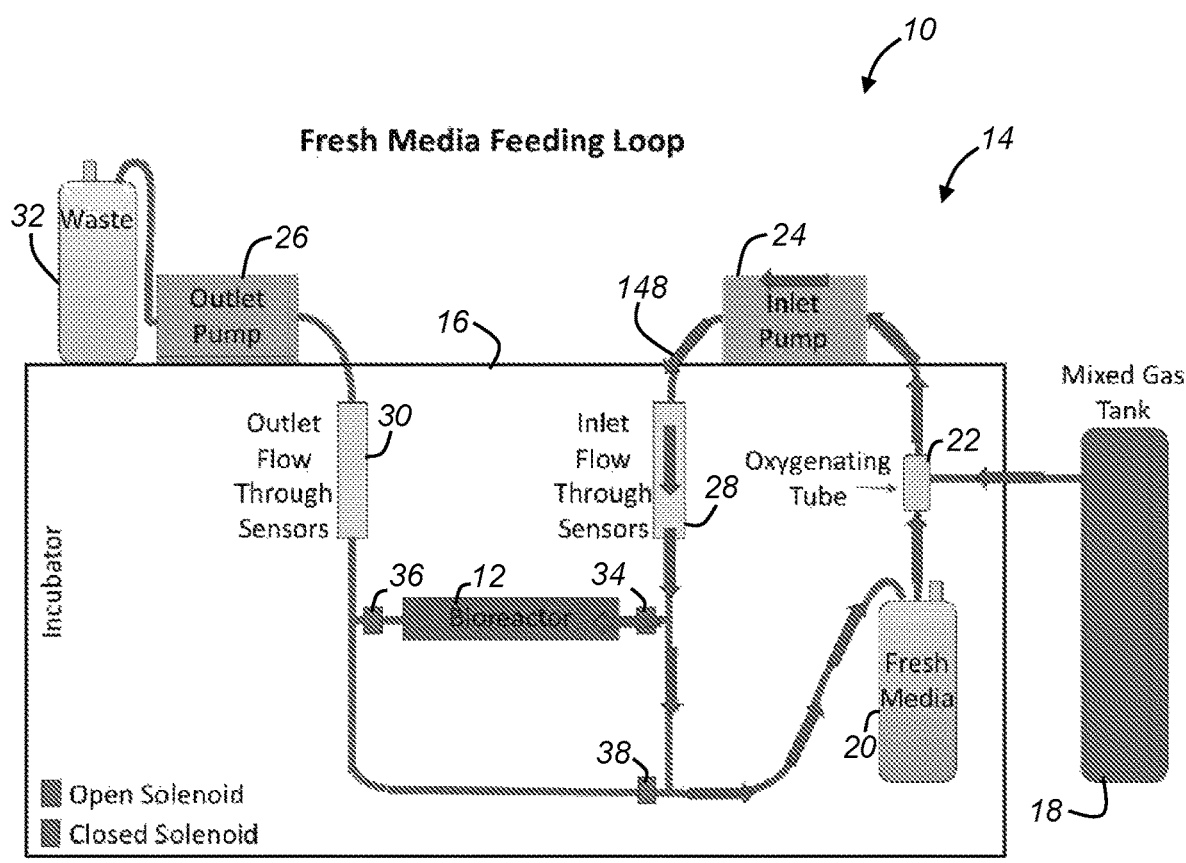

FIG. 3 schematically illustrates tissue culture substrates that may be used with the bioreactor of FIGS. 1 and 2;

FIG. 4 is a perspective view of a first tissue culture side of a bioreactor according to one embodiment;

FIG. 5 is another perspective view of the first tissue culture side of FIG. 4;

FIG. 6 is a perspective view of a second tissue culture side of a bioreactor in accordance with one embodiment;

FIG. 7 schematically illustrates a sterilization loop for the bioreactor assembly of FIG. 1;

FIG. 8 schematically illustrates a conditioning loop for the bioreactor assembly of FIG. 1;

FIG. 9 schematically illustrates a waste media removal loop for the bioreactor assembly of FIG. 1; and FIG. 10 schematically illustrates a fresh media feeding loop for the bioreactor assembly of FIG. 1.

DESCRIPTION

A bioreactor capable of producing complex three-dimensional tissue constructs, such as the bioreactor described herein, can promote the accessibility and availability of a diverse array of tissue constructs for various treatment and research purposes. Given that the bioreactor is structured to produce complex three-dimensional tissue constructs, there can be unique challenges when it comes to issues such as media transfer. The bioreactor disclosed herein facilitates improved media transfer through the use of various ports and other features detailed further below. Improved media transfer can promote tissue formation. Further, the bioreactor assembly has increased controllability with regard to exposure to the external environment.

Complex three-dimensional tissue constructs can include multiple tissue constructs formed from multiple cell sources, and more particularly, complex three-dimensional tissue constructs can include multi-phasic tissue constructs that include multiple tissue constructs cultured from cell sources with one or more of the cell sources containing different cell types e.g., bone and ligament cells). The bioreactor can allow for cells of two or more different sources to be grown independently and then co-cultured to fabricate a scaffold-free, multi-phasic three-dimensional engineered tissue with two or more different types of tissue in the final product. The bioreactor can be a stand-alone culture device or part of an assembly that comprises numerous bioreactors and a perfusion system, as detailed further herein, for example. The bioreactor can allow for the formation of continuous, multi-phasic tissue constructs without any internal manipulation by the technician, thereby minimizing contamination risk. In addition to minimizing contamination risk, a closed bioreactor system can precisely control and maintain the tissue culture environment. Tissue growth and development is highly responsive to environmental factors (pH, temperature, nutrient concentration, etc.), and as such, the entire fabrication process can impact the integrity of the final product. The bioreactor disclosed herein can facilitate such an improved fabrication process, and advantageously, the complex three-dimensional tissue construct can remain in a closed or partially closed environment until it is ultimately needed for patient or researcher use. Through the elimination of manual, user-dependent processes, the bioreactor and method facilitate an automated system and process that can eliminate user variability and that promotes tissue construct consistency. Tissue manufacturing times may be reduced, and production capacity may be increased. Further, the system may be modular, capable of incorporating multiple bioreactors into a larger centrally controlled assembly while, in some embodiments, maintaining a relatively small overall volume to minimize the space required to manufacture the tissue constructs.

FIG. 1 schematically illustrates a bioreactor assembly 10 having a bioreactor 12 and perfusion system 14. The perfusion system 14 is used for temperature control and/or media transfer within the bioreactor 12. In an advantageous embodiment, the perfusion system 14 includes pH, temperature, and dissolved oxygen level monitoring. The bioreactor 12 and various components of the perfusion system 14 are located within an incubator 16 to help control the temperature and various other qualities external to the bioreactor 12. Various performance attributes of the bioreactor assembly 10 and example methods of operation are detailed further below, but in this embodiment, the perfusion system 14 of the bioreactor assembly 10 includes fresh media sources (e.g., a mixed gas tank 18 and a fresh liquid media source 20), an oxygenating tube 22, inlet and outlet pumps 24, 26, inlet and outlet flow through sensors 28, 30, a waste receptacle 32, and various valves 34, 36, and 38. Other sensors, valves, seals, gaskets, etc., not particularly illustrated are certainly possible, including but not limited to pH and oxygen sensors integrated with the bioreactor 12 which communicate with a sensor transmitter 40. As will be detailed below, some sensors, such as the pH sensor and/or oxygen sensor, can be implemented in the port assembly of the bioreactor 12. A load sensor, such as an optical load sensor, could also be used in the bioreactor itself to help measure forces and facilitate removal of the graft. These features of the assembly 10 and perfusion system 14 can help regulate the contents and transfer of media within the bioreactor 12, in conjunction with a computer or controller. Media can include various suspensions, cell sources, liquids and/or gases and will likely vary depending on the desired complex three-dimensional tissue construct to be formed in the bioreactor. Additionally, in the bioreactor assembly 10, it is possible to include several bioreactors 12 that are connected in parallel to a single manifold system and the perfusion system 14.

FIG. 2 is a cross-section view of the bioreactor 12 (only select reference numerals are included in FIG. 2 for clarity purposes). The bioreactor 12 includes a first tissue culture side 42 and a second tissue culture side 44. When the tissue is fully enclosed between the first and second tissue culture sides 42, 44, the bioreactor 12 can be used as a container for tissue preservation, storage, and shipping. Thus, the multi-phasic tissue construct can be preserved within the device so that it can be stored and opened when needed by the surgeon. The bioreactor 12 may be made from an FDA compliant plastic by techniques such as injection molding, stretch blow molding, or machining. In one embodiment, the bioreactor 12 is made from polystyrene, although other materials are possible, such as polycarbonate. Advantageously, the first and second tissue culture sides 42, 44 of the bioreactor 12 are transparent, Which allows a technician to view tissue growth during the culturing process.

The first tissue culture side 42 acts as a base for culturing a first cell source (e.g., bone cells), while the second tissue culture side 44 acts as a lid. When the bioreactor 12 is inverted, the second tissue culture side 44 acts as a base for culturing a second cell source (e.g., ligament cells), while the first tissue culture side 42 acts as a lid. In an advantageous embodiment, the bioreactor 12 is used for the fabrication of scaffold-free bone-ligament-bone (BLB) multi-phasic tissue constructs. However, other cell types can be used, particularly those that form a spontaneously delaminating tissue monolayer or those that are capable of substrate controlled tissue monolayer delamination (e.g., muscle tissue, nerve tissue, etc.). Many cell culture bioreactors are designed for non-adherent cell suspension or cell expansion, but it should be understood that these devices do not provide the means of capturing and co-culturing delaminated monolayers of multiple tissue types required for the formation of multi-phasic tissue constructs, such as BLB tissue constructs. Further, it is possible to have more tissue culture sides than what is illustrated herein, which can be used to fabricate other multi-phasic tissue constructs.

The first tissue culture side 42 and the second tissue culture side 44 generally define an interior area 46 where the tissue construct is formed. The interior area 46 is generally shielded from the external environment, with the exception of external ports 48, 50, 52 which may be a part of a port assembly 54, which is detailed further below. External surfaces 56, 58 of the respective sides 42, 44 are exposed to the external environment on the outside of the bioreactor 12. Regulating the environment within the interior area 46 can help promote multi-phasic tissue construct formation at a first tissue culture support region 60 associated with the first tissue culture side 42 and at a second tissue culture support region 62 associated with the second tissue culture side 44.

The first tissue culture support region 60 includes a first tissue culture support surface 64, and the second tissue culture support region 62 includes a second tissue culture support surface 66. The first tissue culture support surface 64 is a recessed area that supports separate tissue culture plates 68, 70, and the second tissue culture support surface 66 supports a separate tissue culture plate 72. Interiorly extending tissue guides 74, 76, 78, 80 facilitate tissue construct transfer within the interior area 46 of the bioreactor 12.

FIG. 3 more particularly shows that the tissue guides 74-80 are installed in distinct and separate plates 68, 70, 72, which are then placed onto their respective tissue culture support surfaces 64, 66 within the bioreactor 12. It is possible in some embodiments, however, for tissue culturing to take place directly on the support surfaces 64, 66, or on a different form of substrate. In the illustrated embodiments, two tissue constructs of the first tissue type may be formed on the plates 68, 70, and then the bioreactor may be flipped, inverted, turned, or otherwise rotated so as to allow the second tissue construct of a second tissue type to form between the two tissue constructs of the first tissue type on the plate 72. If desired, a non-adherent barrier may be included between the plates 68, 70, which can be made from silicone, Teflon, or another material that does not allow for significant cell adhesion. The plates 68, 70, 72 can be constructed from a sterile polystyrene culture surface that may be coated with growth factors or cell adhesion proteins such as laminin. The addition of cell adhesion proteins can facilitate adherent cell culturing.

The interiorly extending tissue guides 74-80 are rigid pins that at least partially extend (or in this embodiment, wholly extend) into the interior area 46 and between the first tissue culture side 42 and the second tissue culture side 44. The interiorly extending tissue guides 74-80 may be alternately configured than what is illustrated herein. For example, they could be less rigid structures such as sutures, more pronounced rigid structures, or any other form of leg, translation mechanism, guide structure, etc. capable of facilitating translation of a tissue construct thereon. There may be more or less plates and/or guides than what is illustrated herein, as the illustrated embodiment is only an example. The tissue guides 74-80 extend through each of the plates 68-72 such that an exposed portion 82 is situated on the side of each plate that is oriented away from the interior area 46 and more toward the external surfaces 56, 58 of the bioreactor 12 (the exposed portions 82 are visible in FIG. 3 but not in FIG. 2), As will be detailed further below, the bioreactor 12 may include various features to help accommodate the exposed portions 82 and better balance the plates 68-72 within the bioreactor 12. In yet other embodiments, there may not be exposed portions 82, as it is possible to fully integrate the tissue guides 74-80 with the plates 68-72 or directly with the tissue culture support surfaces 64, 66.

The tissue guides 74-80 are angled such that the distance between them is greater at the plates 68, 70 than at the plate 72. This allows for a first construct to slide up and shorten in length until it reaches the plate 72 during translation due to tension developed by the cells in the construct. In one embodiment, after the first tissue construct reaches its position near the plate 72, the bioreactor 12 is flipped to seed cells on the plate 72 that will delaminate and capture the first tissue construct, thereby forming a complex three-dimensional tissue construct or a multi-phasic tissue construct. The distance between the tissue guides may be fixed depending on the specifications of the graft. In the embodiment illustrated in FIGS. 2 and 3, the guides 74-80 are spaced to form two bone constructs, and when the bioreactor 12 is flipped, a ligament tissue construct can form between the two bone constructs. In this particular embodiment, the two bone plates 68, 70 are seeded with cells until they form a monolayer that rolls up and is captured onto the guides 74-80, During this time, the plates 68, 70 are fed with growth media and the bioreactor 12 is base side down with the first tissue culture side 42 acting as a base and the second tissue culture side 44 acting as a lid. At this point, the bone is fed with a differentiation media and the passive tension in the bone constructs will allow for translation on the angled guides 74-80. The bioreactor 12 is filled all the way with liquid media and inverted to facilitate translation down the tissue guides 74-80 onto plate 72. Then, the ligament plate 72 is seeded with cells and a monolayer forms on the plate. Eventually, the ligament is captured on the same guides 74-80 as the bone. The bone-ligament-bone (BLB) tissue construct is then in culture for a period of time to allow for proper stiffness to be achieved.

As described above, a complex three-dimensional tissue construct includes two or more tissue constructs cultured from two or more cell sources. The cell sources may include the same cell type. In another embodiment, the complex three-dimensional tissue construct is a multi-phasic tissue construct which includes two or more tissue constructs cultured from two or more cell sources, with the cell sources having one or more different types of cells, such as the BLB construct described above. Applications of the formed constructs include repair of rotator cuff or anterior cruciate ligament injuries, to cite a few examples. In an advantageous embodiment, mesenchymal stem cells are used for the first and/or second cell source.

FIGS. 4 and 5 show various perspective views of the first tissue culture side 42. In this embodiment, the first tissue culture support surface 64 in the first tissue culture support region 60 is a doubly recessed area that includes a port side wall 84 having port openings 86 that recesses the tissue culture support surface 64 away from a sloped media support surface 88. Two media collection reservoirs 90, 92 are recessed from the tissue culture support surface 64. When the tissue culture plates 68, 70, 72, shown in FIG. 3, are installed within the bioreactor 12, the media collection reservoirs 90, 92 are situated below the plates 68, 70. This provides space for exposed areas 82 of the guides 74-80 and allows for the plates 68, 70 to sit more stably on the tissue culture support surface 64. The media collection reservoirs 90, 92 are also connected to media channels 94, 96 to help empty media from each respective reservoir 90, 92. Without the channels 94, 96, media could undesirably pool in each reservoir 90, 92 without sufficient drainage. Corner projections 97 can also be included to help stabilize, position, and/or hold the tissue culture plates 68, 70 when they are installed within the bioreactor 12.

The sloped media support surface 88 also improves media transfer and drainage within the bioreactor 12 and helps prevent media pooling in the corners of the bioreactor. Advantageously, the sloped media support surface 88 is located on the initial base culture side 42 of the bioreactor 12, which is in culture longer than the tissue culture side 44 (in this embodiment, the bone is in culture longer than the ligament, but this could be adapted depending on the desired tissue construct to be formed). The sloped media support surface 88 converges toward the tissue culture support surface 64 at the tissue culture support region 60. In this particular embodiment, the sloped media support surface 88 has four angled walls 98, 100, 102, 104 extending from a lid recess 106 to the port sidewall 84 at the tissue culture support surface 64. The angled walls 98-104 are more clearly shown in FIGS. 4 and 5; however, FIG. 2 shows the angle θ of each sidewall. Advantageously, this angle θ is the angle of each angled wall 98-104, which is between 3° and 10° (with angles in this range improving media transfer). In a particularly advantageous embodiment, which is illustrated herein, the angle θ is about 5°, or more particularly The bioreactor 12 includes a port assembly 54 having a number of ports that help facilitate media transfer within the internal area 46 of the bioreactor. Ports are schematically illustrated by dotted lines in the figures for example purposes, and are not necessarily to scale. Moreover, the size, shape, configuration, etc. of the ports in the port assembly 54 may vary from what is schematically illustrated in the figures. Further, the configuration of the port assembly 54 is different in FIG. 2 as compared to the other figures. As shown in FIGS. 4 and 5, seeding ports 108, 110 are external ports that extend from the external surface 56 to the port side wall 84 in the tissue culture support region 60. The seeding ports 108, 110 are located closer to the sloped media support surface 88 such that cells from the first cell source can be deposited on plates 68, 70 when they are situated within the bioreactor 12. Feeding ports 112, 114, 116, 118 are also external ports that extend from the external surface 56 to the port side wall 84 in the tissue culture support region 60. The feeding ports 112-118 are located further from the sloped media support surface 88 than the seeding ports 108, 110, and closer to the tissue culture support surface 64. This permits growth media to be fed under plates 68, 70 when installed in the bioreactor 12 such that the ports 112-118 are liquid inlets when the bioreactor is in a base side down orientation. The feeding ports 112-118 are situated in pairs 112, 114 and 116, 118 such that feeding for each well/plate 68, 70 has one port 112, 116 for feeding media in and one port 114, 118 for letting media out.

Additionally, the feeding ports 112-118 serve as gas outlets to relieve pressure when the bioreactor 12 is in a base side up orientation (e.g., the bioreactor 12 flips). Thus, the feeding ports 112-118 have a secondary purpose, as each interior port opening 86 of the ports 112-118 are flush with the uppermost point in the bioreactor interior area 46 when the bioreactor 12 is flipped (i.e., the second side or lid side 44 is down). This is useful for pressure relief and removing gas while feeding the second tissue culture support region 62, because as liquid media enters the internal area 46, gas goes to the top and needs to exit somehow. Accordingly, with reference to the second tissue culture side 44 or lid side shown in FIG. 6, there is a pair of feeding ports 120, 122, These external feeding ports 120, 122 are liquid inlets for feeding media from the external environment at surface 58 to the second tissue support region 62 when the bioreactor 12 is in a base side up/lid side down orientation, but the ports 120, 122 are gas outlets when the bioreactor 12 is in a base side down orientation/lid side up orientation. Unlike the ports 112-118, the ports 120, 122 shown in FIG. 6 open from the external surface 58 into a perimeter channel 123.

Returning to FIGS. 4 and 5, the port assembly 54 also includes internal ports 124, 126 for housing a pH sensor 128 and/or an oxygen sensor 130. Unlike external ports 108-118 which extend from the external surface 56 all the way to the tissue culture support region 60, the internal ports 124, 126 extend from the external surface 56 only partly into the body of the first tissue culture side 42. Internal ports may also be included on the second tissue side 44 if desired. Advantageously, internal ports 124, 126 are used for non-invasive sensors 128, 130 and do not traverse the whole wall. As will be detailed further below, a number of valves (e.g., valves 34, 36, 38) or a valve system may be used to control the opening of, and media flow through, the ports in the port assembly 54. Further, other port configurations, types, numbers of ports, etc., may be included in the port assembly 54.

A lid recess 106 may be included in some embodiments to accommodate the extending ridge 132 on the second tissue culture side 44 (lid recess 106 is shown in FIGS. 4 and 5, and ridge 132 is shown in FIG. 6). This configuration may not be included, as it could be possible to have other configurations such as snapping the two sides 42, 44 together. In the illustrated embodiments, the lid recess 106 helps prevent media from leaking. No matter which side 42, 44 is facing up, the media can fill the entire interior area 46 without escaping. Additionally, the second tissue culture side 44 includes media collection reservoirs 134, 136 that help accommodate the exposed portion 82 of the tissue guides 74-80 in the plate 72 when the tissue culture plates are installed in the bioreactor 12. As with the first side, the media collection reservoirs 134, 136 are connected to respective media channels 138, 140 to facilitate drainage of media from the reservoirs. The media channels 138, 140 connect to the perimeter channel 123 to facilitate media transfer to the ports 120, 122.

As described above, the bioreactor assembly 10 can be selectively controlled in various modes to facilitate media transfer with respect to the bioreactor 12 and/or the port assembly 54. FIG. 7 illustrates with arrows a sterilization loop 142. In this method of operation, the valves 34, 36, are closed, whereas the valve 38 is open. The valves 34, 36, 38 are advantageously electronically controlled solenoids, although it is possible to include other valve types, more valves than what are shown, and different valve configurations. With the sterilization loop 142, the liquid media is a sterilization media, whereas with other loops, the sterilization media may be replaced with a growth and/or differentiation media, to cite two examples. Both the inlet pump 24 and the outlet pump 26 can be driven during the sterilization loop 142. FIG. 8 illustrates with arrows a bioreactor conditioning loop 144 where all of the valves 34, 36, 38 are closed. The inlet pump 24 is driven in this loop 144 while the outlet pump 26 is not. The conditioning loop 144 may be performed after the sterilization loop 142, and may be used to establish proper parameters of the fresh media within the bioreactor assembly (e.g., adequate PH, oxygen levels, temperature, etc.). FIG. 9 illustrates with arrows a waste media removal loop 146 where the valves 34, 38 are closed and the valve 36 is open. The outlet pump 26 is driven in the loop 146 while the inlet pump 24 is not. The waste media removal loop 146 may be used in conjunction with a fresh media feeding loop 148 shown in FIG. 10 to cycle growth and/or differentiation media through the assembly 10. FIG. 10 illustrates with arrows the fresh media feeding loop 148 where the valves 36, 38 are closed and the valve 34 is open. The inlet pump 24 is driven in the loop 148 while the outlet pump 26 is not. The loops 142, 144, 146, 148 can be variously cycled and used during the tissue culture process. Cycling and/or using loops 142, 144, 146, 148 can depend on the culture status, the types of tissue being cultured, etc.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms for "example," "e.g.," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation. In addition, the term "and/or" is to be construed as an inclusive OR. Therefore, for example, the phrase "A, B, and/or C" is to be interpreted as covering all the following: "A"; "B"; "C"; "A and B"; "A and C"; "B and C"; and "A, B, and C."

The invention claimed is:

1. A bioreactor, comprising:
an external surface;
a first tissue culture side for culturing a first cell source in a first tissue culture support region, wherein the first tissue culture support region includes a first tissue culture support surface that supports two or more separate tissue culture plates, and wherein two media collection reservoirs are situated below the two or more separate tissue culture plates;
a second tissue culture side for culturing a second cell source in a second tissue culture support region, wherein the second tissue culture support region includes a second tissue culture support surface that supports a single tissue culture plate; and
a plurality of ports, wherein at least one of the ports of the plurality of ports extends from the first tissue culture support region of the first tissue culture side to the external surface.

2. The bioreactor of claim 1, wherein the plurality of ports includes an external port that is configured to be a liquid inlet when the bioreactor is in a first orientation and a gas outlet when the bioreactor is in a second orientation.

3. The bioreactor of claim 2, wherein the external port opens from the external surface into a perimeter channel.

4. The bioreactor of claim 1, wherein the first tissue culture side and the second tissue culture side are made from a transparent plastic material.

5. The bioreactor of claim 1, wherein the two media collection reservoirs include corner projections to help stabilize or position the two or more separate tissue culture plates.

6. The bioreactor of claim 1, wherein the two or more separate tissue culture plates are joined to the single tissue culture plate with a plurality of interiorly extending tissue guides.

7. The bioreactor of claim 6, wherein the interiorly extending tissue guides are angled such that a distance between the interiorly extending tissue guides is greater at the two or more separate tissue culture plates than a distance between the interiorly extending tissue guides at the single tissue culture plate.

8. The bioreactor of claim 1, wherein the first tissue culture support surface is a doubly recessed area that includes a port side wall having port openings from the plurality of ports.

9. The bioreactor of claim 1, wherein the plurality of ports includes an internal port that extends partly into the first tissue culture side or the second tissue culture side to house a non-invasive sensor.

10. The bioreactor of claim 1, wherein the first tissue culture side includes a lid recess to accommodate an extending ridge on the second tissue culture side.

11. A bioreactor, comprising:
an external surface;
a first tissue culture side for culturing a first cell source in a first tissue culture support region, wherein the first tissue culture support region includes a first tissue culture support surface;
a second tissue culture side for culturing a second cell source in a second tissue culture support region, wherein the second tissue culture support region includes a second tissue culture support surface; and
a plurality of ports, wherein at least one of the ports of the plurality of ports extends from the first tissue culture support region of the first tissue culture side to the external surface, wherein the first tissue culture support surface is a doubly recessed area that includes a port side wall having port openings from the plurality of ports, and wherein the port side wall recesses the first tissue culture support surface away from a sloped media support surface.

12. The bioreactor of claim 11, wherein the sloped media support surface has four angled walls that converge toward the first tissue culture support surface.

13. The bioreactor of claim 12, wherein an angle of each angled wall of the four angled walls is between 3° and 10°, inclusive.

14. The bioreactor of claim 11, wherein the plurality of ports includes feeding ports and seeding ports, and the seeding ports are located closer to the sloped media support surface than the feeding ports.

* * * * *